(12) United States Patent
Zirps et al.

(10) Patent No.: US 7,717,846 B2
(45) Date of Patent: *May 18, 2010

(54) EXTERNAL ENDOSCOPIC ACCESSORY CONTROL SYSTEM

(75) Inventors: Christopher T. Zirps, Sharon, MA (US); Timothy R. Membrino, Acton, MA (US); David J. Copeland, Milton, MA (US); Sean J. Silva, North Reading, MA (US); Eric Mears, South Bristol, ME (US); Joseph Logan, Trumbull, CT (US); Stephen J. Yardan, Branford, CT (US)

(73) Assignee: C.R. Bard, Inc., Murray Hill, NJ (US)

( * ) Notice: Subject to any disclaimer, the term of this patent is extended or adjusted under 35 U.S.C. 154(b) by 457 days.

This patent is subject to a terminal disclaimer.

(21) Appl. No.: 11/787,850

(22) Filed: Apr. 18, 2007

(65) Prior Publication Data

US 2007/0191674 A1 Aug. 16, 2007

Related U.S. Application Data

(63) Continuation of application No. 10/656,085, filed on Sep. 5, 2003, now Pat. No. 7,223,230.

(60) Provisional application No. 60/408,594, filed on Sep. 6, 2002.

(51) Int. Cl.
*A61B 1/00* (2006.01)

(52) U.S. Cl. .................. 600/104; 600/102; 600/127; 600/129; 600/131; 606/1; 606/170; 606/205

(58) Field of Classification Search ............... 600/101, 600/104, 107, 131, 153
See application file for complete search history.

(56) References Cited

U.S. PATENT DOCUMENTS 4,226,239 A 10/1980 Polk et al.

(Continued)

FOREIGN PATENT DOCUMENTS

DE 42 42 431 A1 6/1994

(Continued)

OTHER PUBLICATIONS

Supplemental European Search Report for European Application EP 03 79 4639.

(Continued)

*Primary Examiner*—Linda C Dvorak
*Assistant Examiner*—Matthew J Kasztejna
(74) *Attorney, Agent, or Firm*—Wolf, Greenfield & Sacks, P.C.

(57) ABSTRACT

The present invention provides an endoscopic accessory control system that resides externally of the endoscope. The system comprises the endoscopic accessory with a working end to be placed at the distal end of the endoscope, a control sheath extending proximally external to the endoscope and a control handle joined to the proximal end of the control sheath. The control handle is slidably mounted to the exterior surface of the endoscope shaft and is configured to permit grasping of both the shaft and the handle. With the control handle and endoscope shaft grasped with one hand, the other hand of the user is left free to manipulate the endoscope distal tip controls. Additionally, the external arrangement of the control sheath leaves the working channel of the endoscope free for use of accessories or operations.

7 Claims, 10 Drawing Sheets

U.S. PATENT DOCUMENTS

| | | | |
|---|---|---|---|
| 4,230,116 A | 10/1980 | Watson | |
| 4,735,194 A | 4/1988 | Stiegmann | |
| 4,788,966 A | 12/1988 | Yoon | |
| 5,152,278 A * | 10/1992 | Clayman | 600/131 |
| 5,201,908 A | 4/1993 | Jones | |
| 5,259,366 A | 11/1993 | Reydel et al. | |
| 5,275,151 A | 1/1994 | Shockey et al. | |
| D344,334 S | 2/1994 | Dulebohn et al. | |
| 5,325,746 A | 7/1994 | Anderson | |
| 5,356,416 A | 10/1994 | Chu et al. | |
| 5,382,254 A | 1/1995 | McGarry et al. | |
| 5,383,875 A | 1/1995 | Bays et al. | |
| 5,409,478 A | 4/1995 | Gerry et al. | |
| 5,447,148 A | 9/1995 | Oneda | |
| 5,470,328 A | 11/1995 | Furnish et al. | |
| 5,498,256 A | 3/1996 | Furnish | |
| 5,503,616 A | 4/1996 | Jones | |
| 5,507,797 A | 4/1996 | Suzuki et al. | |
| 5,569,268 A | 10/1996 | Hosoda | |
| 5,601,568 A | 2/1997 | Chevillon et al. | |
| D378,611 S | 3/1997 | Croley | |
| 5,624,431 A | 4/1997 | Gerry et al. | |
| 5,643,175 A | 7/1997 | Adair | |
| D383,539 S | 9/1997 | Croley | |
| 5,662,588 A | 9/1997 | Iida | |
| D385,350 S | 10/1997 | Furnish | |
| 5,690,645 A | 11/1997 | Van Erp | |
| 5,725,536 A | 3/1998 | Oberlin et al. | |
| 5,735,793 A | 4/1998 | Takahashi et al. | |
| 5,788,715 A | 8/1998 | Watson et al. | |
| 5,888,191 A | 3/1999 | Akiba | |
| 5,993,384 A | 11/1999 | Lunsford et al. | |
| 6,059,719 A | 5/2000 | Yamamoto et al. | |
| 6,136,009 A | 10/2000 | Mears | |
| 6,149,659 A | 11/2000 | Ahmed | |
| 6,306,081 B1 | 10/2001 | Ishikawa et al. | |
| 6,340,344 B1 | 1/2002 | Christopher | |
| 6,371,973 B1 | 4/2002 | Tepper | |
| D459,474 S | 6/2002 | Bratt et al. | |
| 6,443,944 B1 * | 9/2002 | Doshi et al. | 606/1 |
| 6,471,638 B1 * | 10/2002 | Chang et al. | 600/114 |
| 6,520,954 B2 | 2/2003 | Ouchi | |
| 6,533,797 B1 * | 3/2003 | Stone et al. | 606/184 |
| 6,540,737 B2 * | 4/2003 | Bacher et al. | 606/1 |
| 6,576,005 B1 | 6/2003 | Geitz | |
| D480,807 S | 10/2003 | Yardan et al. | |
| 6,676,668 B2 * | 1/2004 | Mercereau et al. | 606/127 |
| 6,679,834 B2 * | 1/2004 | Stahl et al. | 600/131 |
| 6,685,713 B1 | 2/2004 | Ahmed | |
| 6,786,865 B2 * | 9/2004 | Dhindsa | 600/159 |
| 6,830,545 B2 * | 12/2004 | Bendall | 600/114 |
| 7,223,230 B2 * | 5/2007 | Zirps et al. | 600/104 |
| 2001/0027312 A1 | 10/2001 | Bacher et al. | |
| 2002/0177847 A1 | 11/2002 | Long | |
| 2003/0167062 A1 | 9/2003 | Gambale et al. | |
| 2003/0171651 A1 | 9/2003 | Page et al. | |
| 2003/0171760 A1 | 9/2003 | Gambale | |
| 2003/0208209 A1 | 11/2003 | Gambale et al. | |
| 2003/0212308 A1 | 11/2003 | Bendall | |
| 2004/0034371 A1 | 2/2004 | Lehman et al. | |

FOREIGN PATENT DOCUMENTS

| | | |
|---|---|---|
| JP | 5-307143 | 11/1993 |
| JP | 2000-107192 | 4/2000 |
| JP | 2000-300574 | 10/2000 |
| JP | 2002-143078 | 5/2002 |
| JP | 2003-506129 | 2/2003 |
| WO | WO 2004/021865 A2 | 3/2004 |

OTHER PUBLICATIONS

U.S. Appl. No. 10/656,083, filed Sep. 5, 2003, Zirps et al.
U.S. Appl. No. 10/656,085, filed Sep. 5, 2003, Zirps et al.
U.S. Appl. No. 10/656,557, filed Sep. 5, 2003, Zirps et al.
U.S. Appl. No. 10/658,135, filed Sep. 8, 2003, Aznoian et al.
U.S. Appl. No. 10/658,619, filed Sep. 8, 2003, Gambale et al.
U.S. Appl. No. 10/847,190, filed May 17, 2004, Gambale et al.
English translation of Japanese Notice of Reasons for Rejection, date of dispatch Sep. 29, 2009, 3 pages.

* cited by examiner

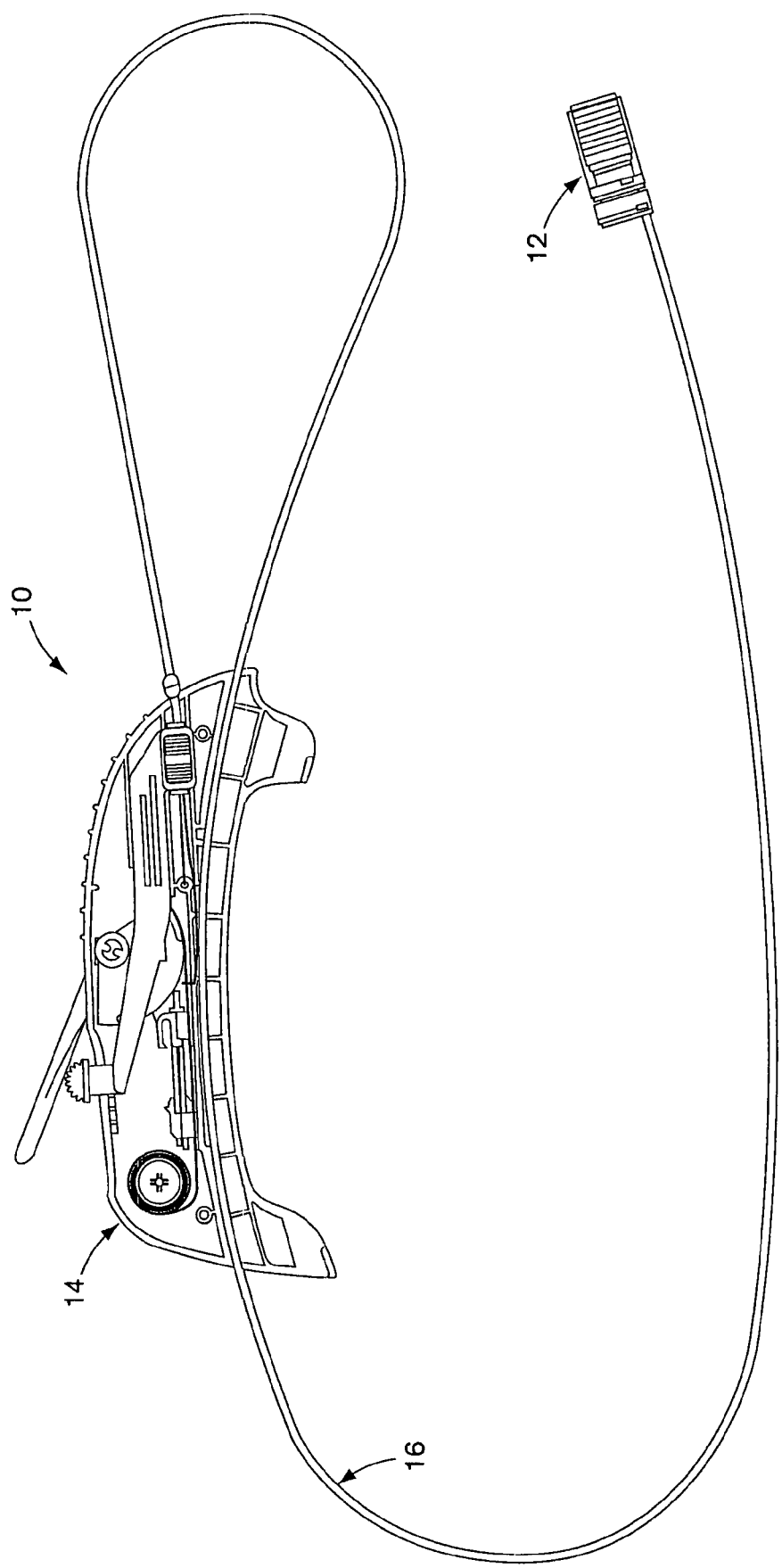

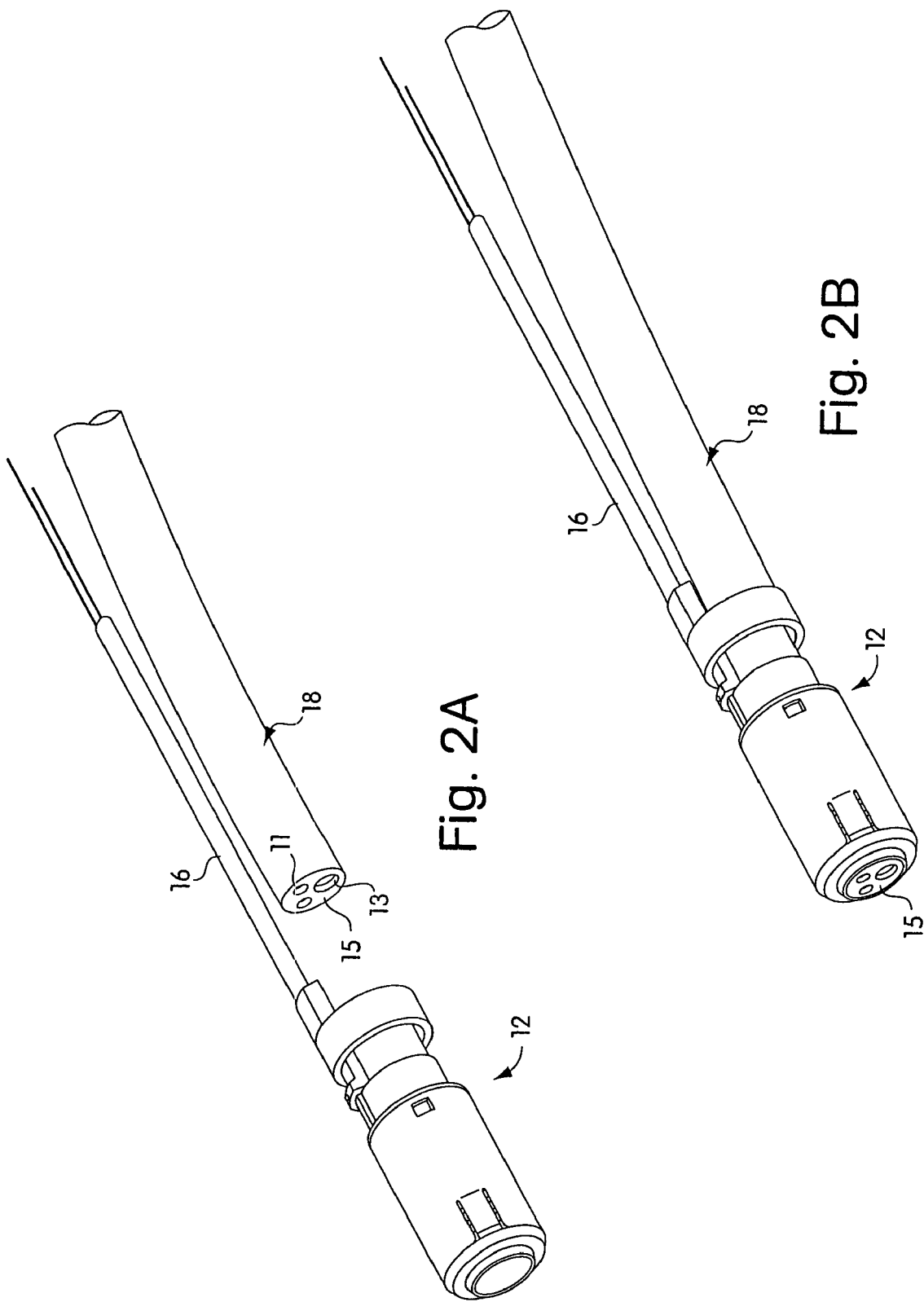

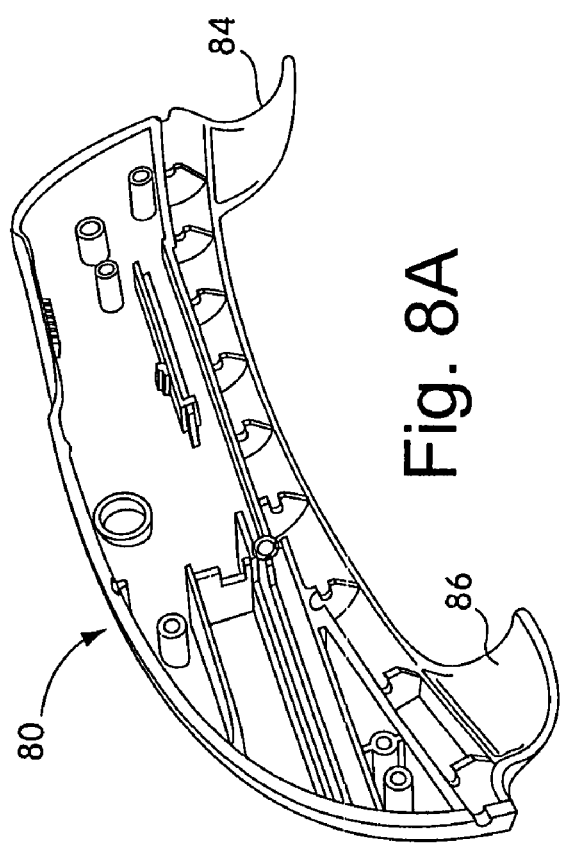
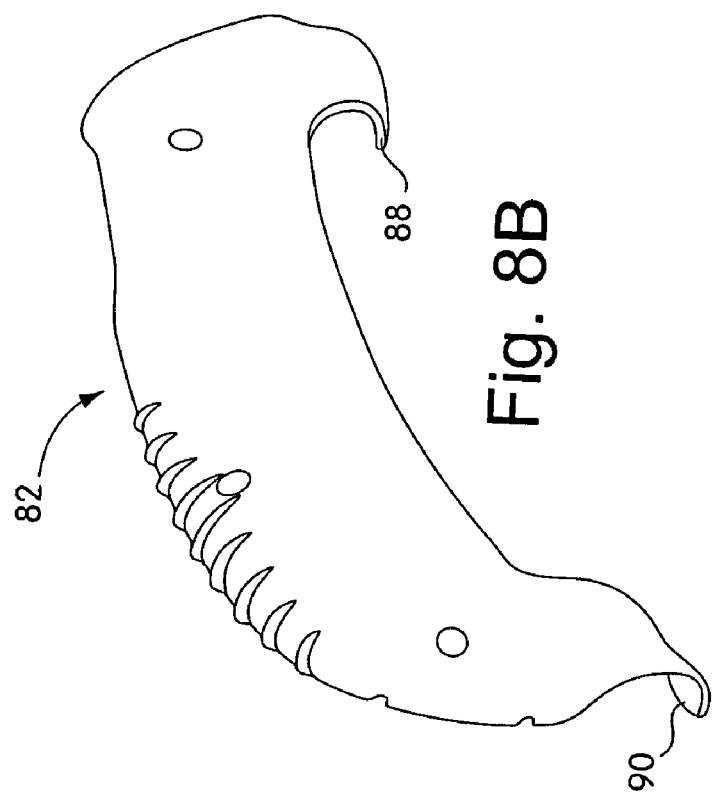

EXTERNAL ENDOSCOPIC ACCESSORY CONTROL SYSTEM

FIELD OF THE INVENTION

The present invention relates to endoscopes, accessory devices used with endoscopes and associated methods. In particular, the present invention is directed to facilitating use of medical devices and endoscopic accessories with an endoscope.

BACKGROUND OF THE INVENTION

Endoscopes are elongate instruments navigable through natural body lumens and cavities of a patient for the purpose of remotely evaluating and treating a variety of ailments. Endoscopes have viewing capability provided by fiber optic elements that transmit images along their length to the medical care provider. Endoscopes may specifically configured in length, diameter, flexibility and lumen configuration to navigate specific treatment areas in the body. Examples of specifically configured endoscopes are a laparoscope, duodenoscope, colonoscope, sigmoidoscope, bronchoscope and urethroscope among others. In combination with remote viewing capability, endoscopes are frequently configured to provide a working channel through which shaft mounted tools and medical instruments may be navigated and remotely operated. Additionally, the endoscope shaft itself may carry a medical instrument for remotely performing a procedure at an internal treatment site, while permitting direct visualization of the site through the endoscope.

Presently, instruments and accessories used with endoscopes employ shafts that extend from the distal working end of the instrument, proximally outside of the patient to provide a mechanism by which the physician can manipulate the device. When used with an endoscope, the instrument shafts are routinely passed through the working channel of an endoscope so that the device extends distally to the distal face of the endoscope while the proximal end extends out through a port in the control handle of the endoscope to provide means for the physician to manipulate the instrument. In the case of certain endoscopic accessories, the distal end of the device attaches directly to the outside surface of the distal end of the endoscope. However, even with accessories that attach to the distal end of the endoscope, control elements such as cables or wires must pass through the working channel of the endoscope.

The arrangement of instruments and accessories passing through the working channel of the endoscope presents several problems to the user operating the combination. First, setting up the device can be cumbersome and time-consuming for the physician. In the use of accessories that attach to the distal end of the endoscope, the physician or technician preparing for the procedure must first back load control elements for the accessory into the working channel of the endoscope. This procedure entails threading the control cables or wires for the accessory into the working channel at the distal end of the endoscope and advancing the wires through until they project from a port at the control handle of the endoscope. After inserting the control elements through the working channel, the accessory may then be secured to the distal end of the endoscope. As a final step in the assembly, an accessory control module that will be manipulated by the physician during the procedure must be connected to the proximal end of the control element and then secured in some fashion to the endoscope control handle. The means for connecting such a control module to the endoscope control handle may be awkward and may not be secure because the accessory may not be designed for the particular endoscope control handle set-up.

After the lengthy set-up procedure described above, another problem faced by the physician during the procedure is controlling both the endoscope and the accessory at the same time. Typically, in an endoscopic procedure performed without an additional accessory, a physician will hold the endoscope control handle in the left-hand while advancing and controlling longitudinal movement of the shaft with the right hand, grasping the shaft along its midportion. When an accessory is added, the proximal control module presents the problem of operating a third element that must be manipulated by the physician's hand during the procedure. Obviously, with only two hands available, a physician must have the assistance of another person to control the endoscope accessory combination during the procedure. Alternatively, the physician will have to release control of one control element in order to manipulate the third element during various portions of the procedure. However, while the endoscope shaft or either the endoscope or accessory controls are released, that element will be subject to small undesired movements that may result in movement of the device away from the intended internal treatment site. It would be desirable to provide a system that permits two-handed control of both the endoscope and the accessory or instrument being used in conjunction with it.

Another disadvantage of current endoscopic accessories and instruments is that their control shafts must pass through a working lumen of the endoscope that could otherwise be used for other purposes during the medical procedure. In order to provide a reasonably small diameter, endoscopes can afford to provide only limited additional space for working channels to accept accessories or provide a lumen for other operations. Accordingly, when the control elements for a single accessory take up the space provided by the working channel, the use of other instruments or procedures through the channel are necessarily hindered or eliminated. With control elements for the accessory extending through the working channel, a second device, such as an injection needle for drug therapy will not be able to pass through the working channel and may, therefore, have to be navigated to the site with a second, subsequent intubation with the endoscope, which increases procedure time and danger to the patient. Additionally, functions such as aspiration are hindered by the presence of control elements in the working channel of the endoscope. With the diameter of the working channel being used predominantly by the indwelling control elements, vacuum through the channel is reduced and the aspirating function impaired. The reduced effectiveness of aspiration can be problematic in applications where blood and tissue may cover the distal end of the endoscope inhibiting viewing capability. Insufficient aspiration may not adequately clear the area of the distal end of the endoscope of tissue debris. Also, debris and blood that is sucked into the channel may interfere with the smooth operation of the accessory control elements. Additionally, procedures that require aspiration to collect areas of tissue into a chamber, such as band ligation or suturing may be negatively impacted by reduced aspiration capacity. Accordingly, it would be desirable to provide an endoscopic accessory control system that does not dominate the use of the endoscope's working channel.

SUMMARY OF THE INVENTION

The present invention provides an endoscopic accessory control system that resides external to an endoscope with which it is used. By remaining external to the endoscope, the control system provides a platform by which a variety of endoscopic accessories and instruments may be quickly and easily applied to any endoscope prior to a procedure.

Mounting of an accessory is facilitated by the present invention because the control elements for the distal operating portion of the accessory are maintained external to the endoscope. Time need not be spent back loading control wires through the working channel of an endoscope. Rather, the distal portion may be quickly affixed to the distal end of the endoscope while control elements lie external to the endoscope extending to a control handle.

The present invention improves control handle placement to facilitate two-handed operation because the accessory control elements do not extend through the working channel. The proximal ends of the accessory control elements need not extend from the working channel proximal port at the endoscope control handle. This permits the accessory control handle to reside at the end of the control elements at any point along the endoscope shaft midportion. Thus, the control handle can be placed at a location where the physician would ordinarily grasp the endoscope shaft to control it. The control handle for the endoscopic accessory is externally mounted to the endoscope shaft, slidable along its length and configured to be grasped by a physician's hand together with the shaft of the endoscope so that both can be controlled simultaneously with the single hand. The ergonomic controls of the handle permit easy manipulation of the accessory control elements by the physician while controlling the position of the handle along the endoscope and controlling movement of the endoscope shaft relative to the patient.

With the control elements for the endoscopic accessory residing externally of the endoscope, the working channel of the endoscope is left open for dedicated functions such as aspiration or injection or for the passage of other instruments that may be useful in a given procedure.

It is an object of the present invention to provide an endoscopic accessory control system that mounts externally to the endoscope shaft to facilitate mounting of the accessory and to avoid utilizing the working channel of the endoscope so that it may be left open for other instruments or operations.

It is another object of the present invention to provide an endoscopic accessory control system that permits two-handed operation of the endoscope and accessory, combination.

It is another object of the invention to provide an endoscopic accessory control system that provides a control handle that permits grasping of the endoscope shaft and operation of the accessory control elements with a single hand.

It is another object of the present invention to provide an endoscopic accessory control system that can serve as a platform by which a wide variety of instruments and operative devices can be used in conjunction with an endoscope.

It is another object of the invention to provide a method operating an endoscope and endoscopic accessory by using one hand to operate endoscope controls at the proximal end of the endoscope and the other hand to operate endoscopic accessory controls positioned on the endoscope shaft between the proximal and distal ends of the shaft.

BRIEF DESCRIPTION OF THE DRAWINGS

The foregoing and other objects and advantages of the invention will be appreciated more fully from the following further description thereof, with reference to the accompanying diagrammatic drawings wherein:

FIG. 1 is a partial sectional illustration of the endoscopic accessory control system of the present invention;

FIG. 2A is an isometric illustration of the distal portion of an accessory and sheath prior to mounting on an endoscope;

FIG. 2B is an isometric illustration of the distal portion of an accessory and mounted on the distal end of an endoscope;

FIGS. 8A and 8B are isometric illustrations of left and right body halves of the control handle assembly.

DESCRIPTION OF THE ILLUSTRATIVE EMBODIMENTS

Figure 1A:
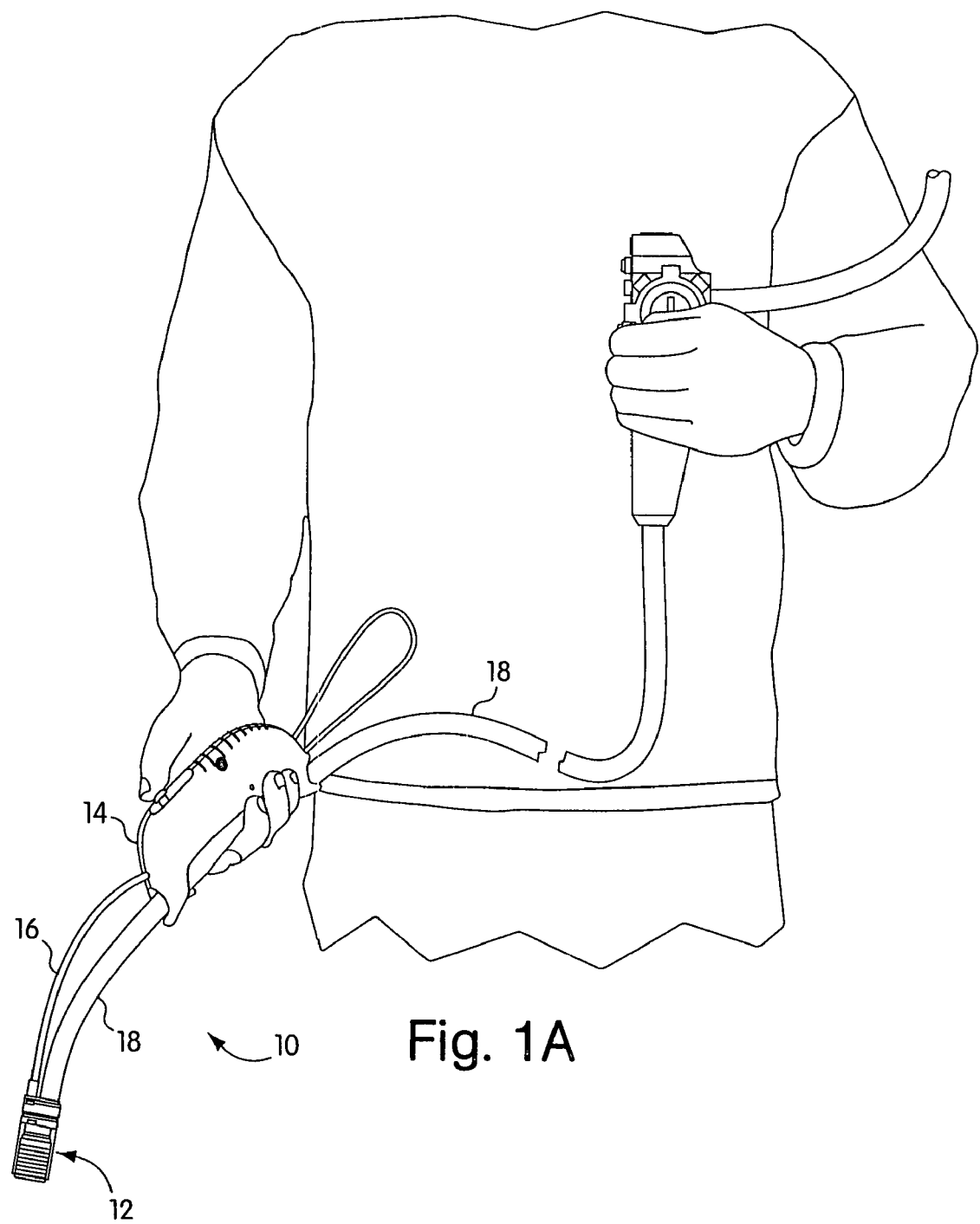
FIG. 1A is an illustration of an operator grasping an endoscope control in the left-hand and the control handle for the system of the present invention in the right hand.

The endoscopic accessory control system 10, shown in FIG. 1, comprises an accessory distal operating portion 12 joined to a control handle 14 via a control sheath 16. The distal portion 12 is removably mounted to the distal end of an endoscope. The distal portion 12 shown in the figures and discussed in the illustrative embodiment is a multiple band endoscopic ligator configured to deliver ligating bands to internal tissue locations, such as at varices in order to prevent bleeding at those sites. It should be understood that other types of accessories such as forceps, cutting instruments or suturing devices could be substituted as the operating component 12 discussed here. The distal portion of the accessory is operated by control wires slidable through sheath 16, which extends proximally, external to the endoscope to the control handle 14. The handle is slidably and removably attached to the exterior of the endoscope shaft.

Figure 1B:
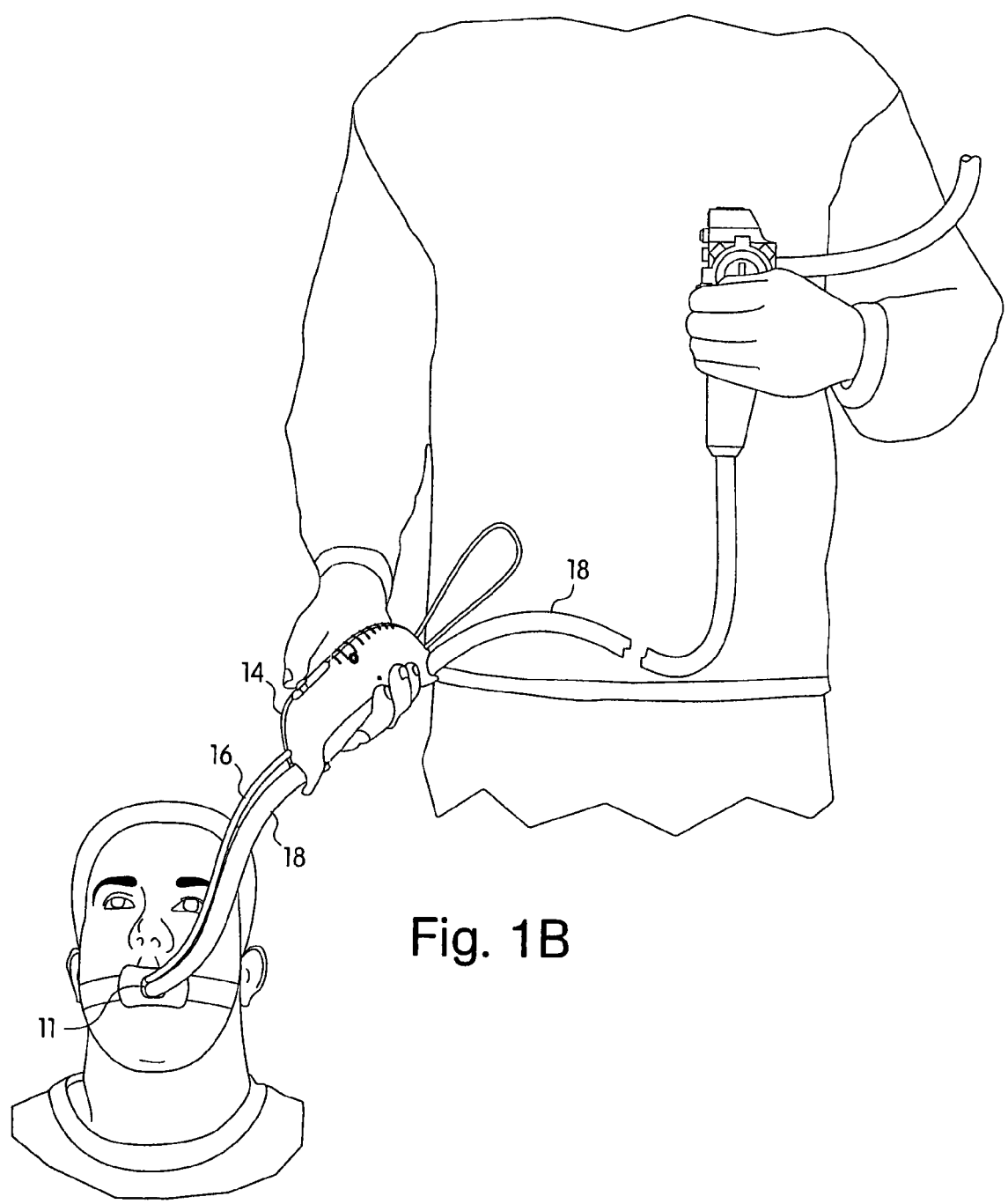
FIG. 1B is an illustration of an operator inserting into a patient an accessory and sheath of the inventive system on mounted on an endoscope.

In an exemplary use of the band ligator device such as treatment of esophageal varices, the distal end of the endoscope 18 with the ligator 12 attached is advanced through a patient's mouth 11 and down the esophagus as shown in FIGS. 1A and 1B. Treatment sites, varices in this example, are located visually with the endoscope. When a varix site is located, the distal end of the flexible endoscope is articulated to navigate the distal face of the scope to the varix location. Vacuum is then applied through the endoscope to gather up a section of tissue surrounding the varix into the ligator and an elastic ligating band is advanced from the ligator device onto and around the gathered tissue to stop bleeding.

The distal portion 12 of the accessory device may be slidably mounted onto a distal end of an endoscope 18 as is shown in FIGS. 2A and 2B. Alternatively the distal portion may be joined to the distal of an endoscope by inserting an element of the distal portion into the working channel of the endoscope. The distal portion 12 is backloaded onto the distal end 18 of the scope and slid proximally so that the distal end of the distal portion is substantially flush with the distal face 15 of the scope. The distal portion 12 of the device is frictionally retained on the endoscope. When the device is mounted to an endoscope 18, the sheath 16 containing control wires and connected to the distal portion, extends parallel to the endoscope shaft, proximally to a control handle 14 as shown in FIGS. 1A and 1B.

Figure 3:
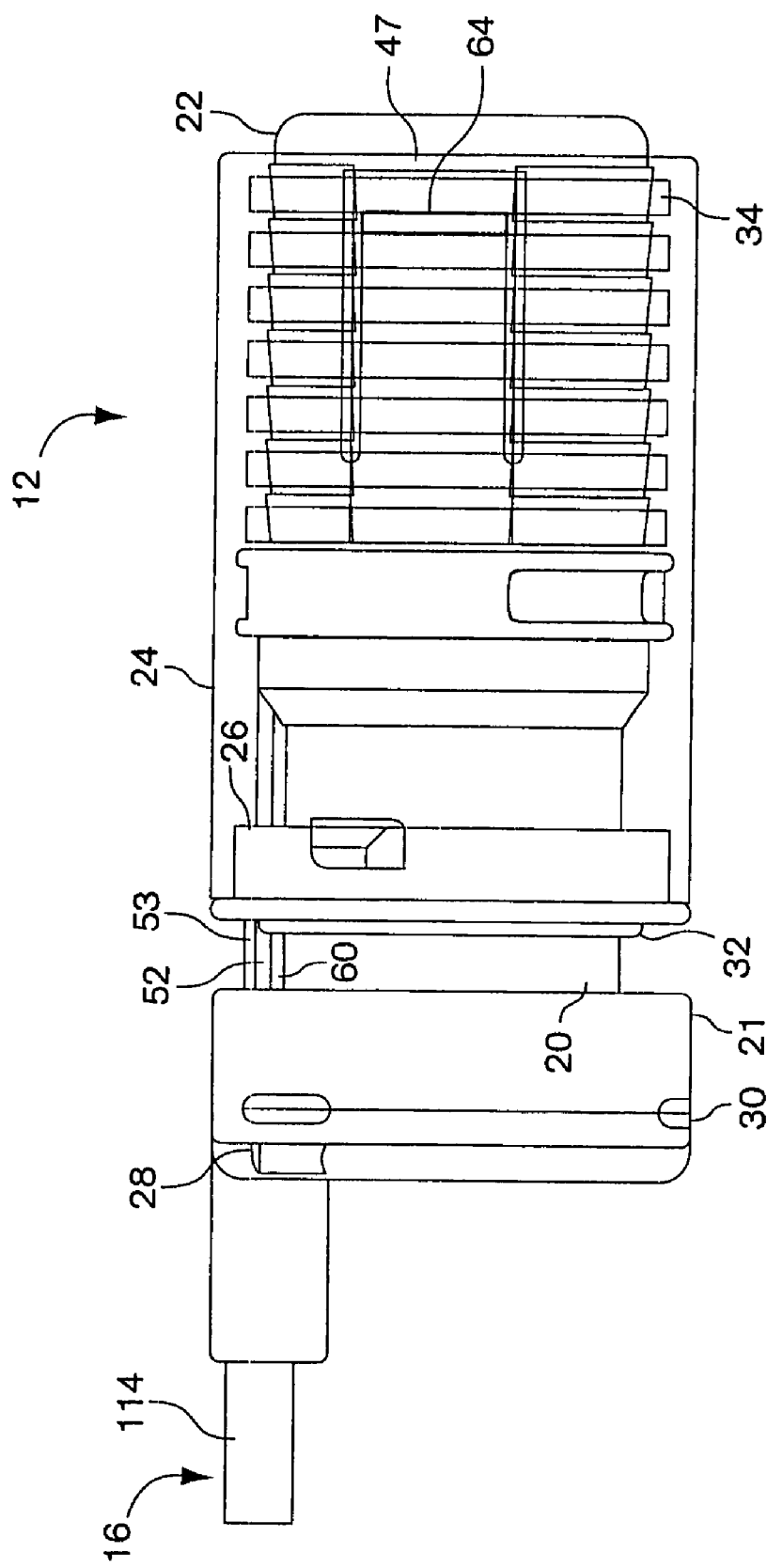
FIG. 3 is a side view of the distal portion of an accessory band ligator.
Figure 4:
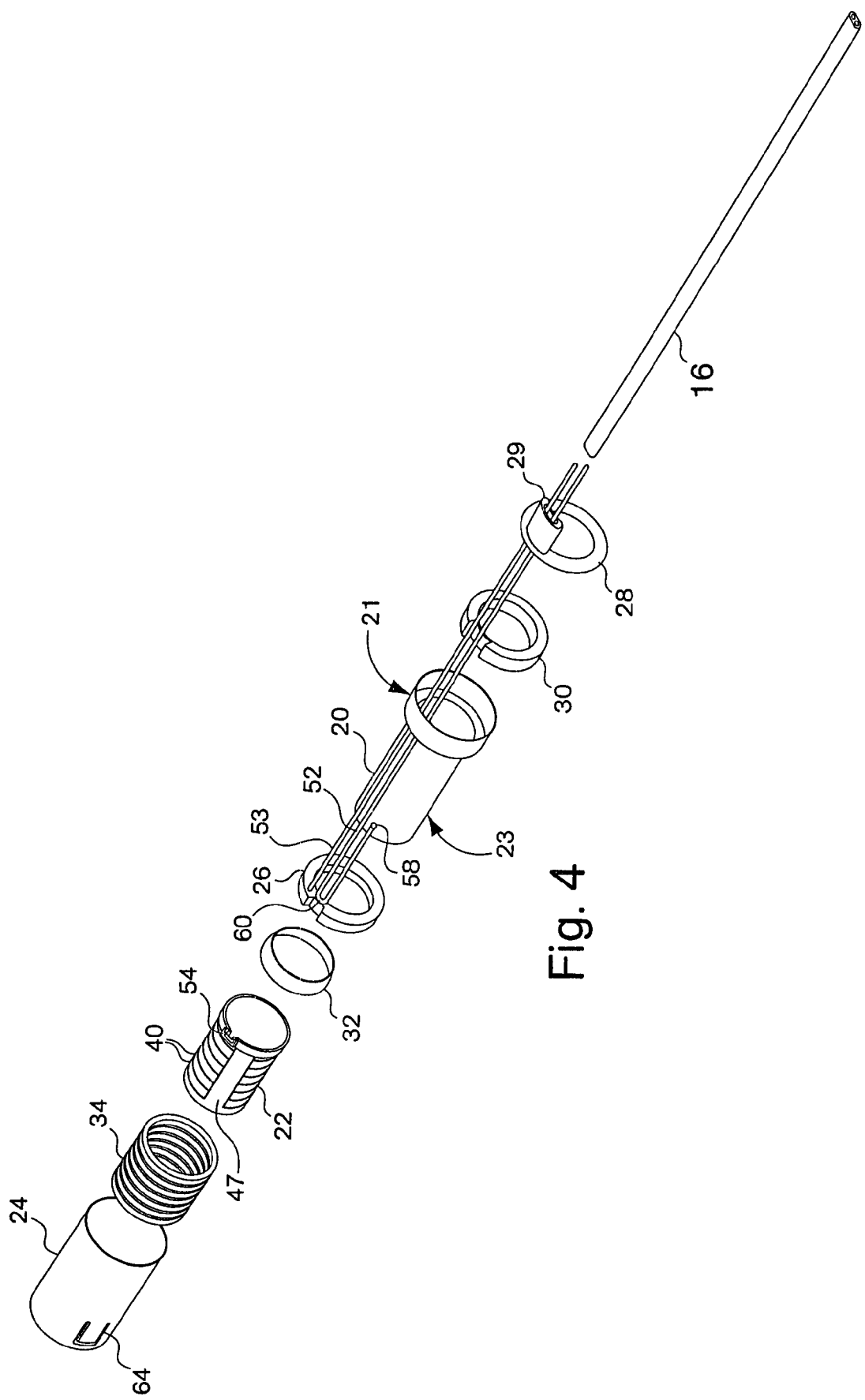
FIG. 4 is an exploded view of the components of the distal portion of an accessory band ligator.

FIG. 3 shows an assembly drawing of the distal portion 12 of an accessory. To illustrate how the distal portion of an accessory of the present inventive system is configured operate and be mounted to an endoscope an example of an accessory configured as a ligating device is presented. An exploded view of the distal portion of the device revealing its individual components is shown in FIG. 4. In the example of a band ligator shown in FIG. 3, the distal portion 12 is comprised of three coaxially arranged tubes: a static sleeve 20 (inner most tube); a band carrier 22 (middle tube) and; a band driver 24 (outer tube). Operation of the device involves relative sliding movement of the tubes to effect band delivery. Movement of the components of the distal portion 12 of the accessory is achieved by manipulation of control elements on the accessory control handle 14.

Figure 5:
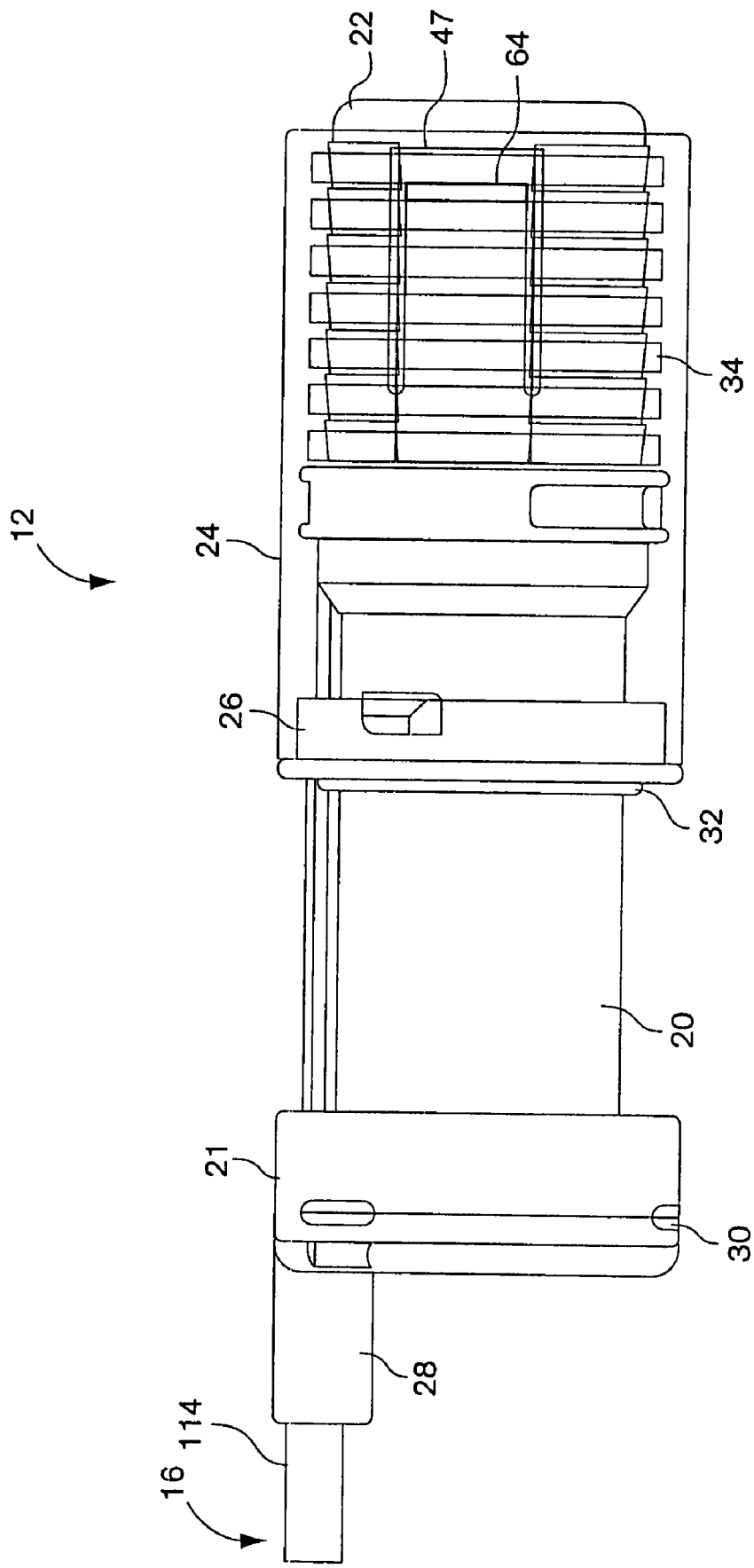
FIG. 5 is a side view of the distal portion of an accessory band ligator with the band carrier and band driver in an extended position relative to the static sleeve.
Figure 6:
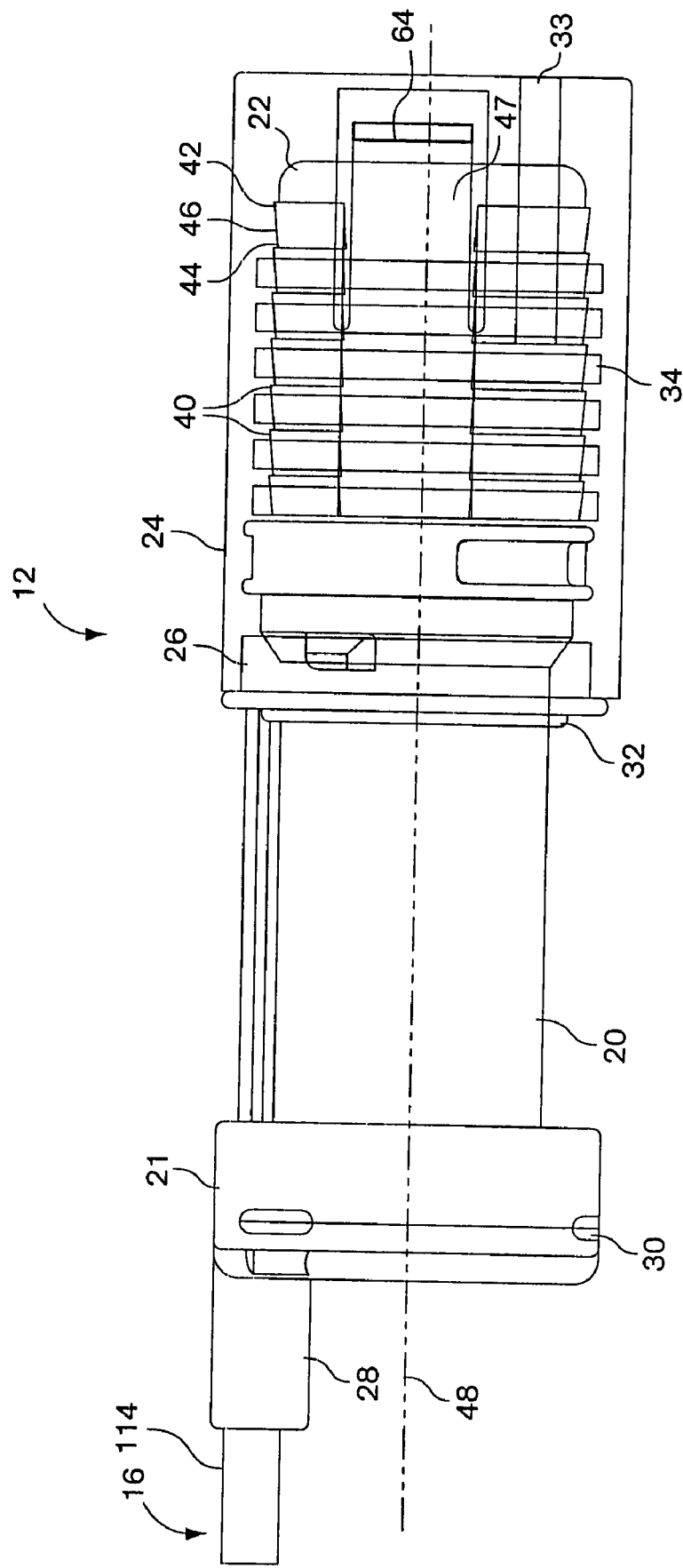
FIG. 6 is a side view of the distal portion of an accessory band ligator with the band carrier extended relative to the static sleeve and the band driver extended relative to the band carrier to discharge a band.

When the device is navigated to a tissue treatment site such as a varix location, the tubes are in a retracted position, such that the band driver 24 and band carrier 22 are positioned proximally on the static sleeve 20. In this position the distal portion 12 does not interfere with the peripheral view through the viewing lens 11 on the distal face 15 of the endoscope (FIGS. 2B and 3). When the varix site has been reached, the band driver 24 and band carrier 22 together are slid distally relative to static sleeve 20 to the position shown in FIG. 5. By their distal movement on the static sleeve, the band carrier 22 and band driver 24 together are extended beyond the distal face of the endoscope. The cylindrical interior of the band carrier creates a vacuum chamber, closed at its proximal end by the endoscope distal face 15 and open at its distal end to receive tissue. Band carrier 22 and driver 24 are preferably made from transparent polymer materials to minimize interference with peripheral viewing through the endoscope when they are advanced beyond the distal face 15. Tissue is aspirated into the vacuum chamber when suction is applied through the vacuum port 13 on the distal face of the endoscope. With the tissue aspirated into the vacuum chamber, the band driver 24 is then slid distally relative to the band carrier 22. Fingers 64 projecting radially inward from the band carrier and engaging the proximal side of the distal most band serve to push a band 34 from the band carrier and onto the tissue (FIG. 6).

The exploded view of the distal portion 12 presented in FIG. 4 shows the arrangement of components that permit the operation of the accessory described above. The static sleeve 20 is the innermost tube and serves as a base member for the assembly of all components that comprise the distal portion of the device. The static sleeve has a small diameter portion 23 that steps up to a large diameter portion 21 at the proximal end of the sleeve. Fitted into the large proximal portion 21 may be an annular vacuum seal 30. A proximal retainer 28 is snap-fit into the enlarged diameter proximal portion 21, capturing the vacuum seal 30 in the assembly. The vacuum seal helps to provide a vacuum tight friction fit for the device onto an endoscope shaft that helps to promote greater suction in the vacuum chamber when the band carrier is extended and vacuum applied. The sheath 16, which houses control wires that lead to the proximally located handle, terminates and is fixed in receptacle 29 of the proximal retainer 28.

Vacuum seal ring 32 is positioned between the outer surface of the static sleeve 20 and the interior surface of the band carrier 22. The presence of the vacuum seal ring between those two cylinders helps to insure that sufficient suction is developed in the vacuum chamber created when the band carrier 22 is slid distally relative to the static sleeve 20 and beyond the distal face 15 of the endoscope to capture tissue.

The band carrier 22 and band driver 24 together may be moved longitudinally relative to the static sleeve 20 by movement of the static control wire 52 distally relative to the sheath 16. The static wire 52 wraps around and is held fixed in U-shaped receptacle 54 formed in rib 56 at the proximal end of the band carrier. As the control wire extends through the U-shaped receptacle, one side of the wire extends proximally back through the sheath 16 to the control handle 14 of the device. The end of the control wire extending through the other side of the U-shaped channel continues proximally slightly to provide an extension 60 that terminates in a ball tip 58. The extension 60 slides through a passage in the static sleeve and proximal retainer 28 large enough for only the wire to pass, but not the ball tip. When the ball tip reaches the passage (not shown), it stops the longitudinal travel of the wire in the distal direction. The remaining length of wire 60 and ball tip 58 correspond in length to the amount of longitudinal travel that the band carrier 22 can have on the static sleeve 20 without becoming disconnected. Thus, the remaining portion of the wire 60 and ball stop 58 comprise a safety limit stop that prevents the band carrier from being overextended during use.

The band driver 24 is slidably received over the band carrier with resilient arms 64 arranged to slide within diametrically opposed channels 47 as discussed above. Band driver retainer 26 is snap-fit into the proximal end of the band driver 24 and fixedly receives driver control wire 53 so that longitudinal movement of the driver relative to the band carrier 22 and static sleeve 20 can be affected from the proximally located handle.

Figure 7:
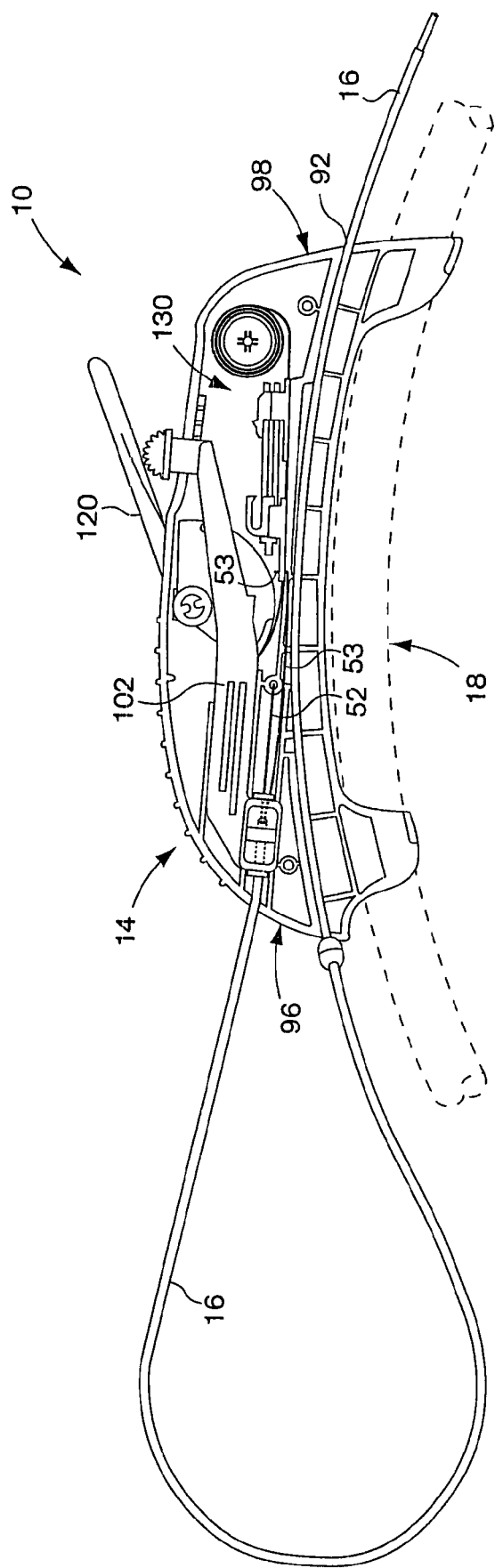
FIG. 7 is a sectional view of the control handle mounted on an endoscope (shown in phantom)

As mentioned above the control sheath 16 carries slidable control wires 52 and 53 each joined to control handle 14 and in particular to operator controls on the control handle, as shown in FIG. 7, that permit a user to manipulate the accessory at the distal end of the sheath. For example, operator controls such as slide 102 and thumb lever 120 may be mounted externally on the control handle 14 and configured to move wire 52 and wire 53 relative to the sheath 16 to cause corresponding relative movement of components of the accessory distal portion 12. In the example of a band ligator described above, movement of the wires relative to each other causes relative longitudinal sliding movement between an inner cylinder band carrier carrying ligating bands and the outer cylinder band driver configured to push bands off of the band carrier as shown in FIGS. 3, 5 and 6. For additional detailed description of how the control wires may be configured with an accessory to accomplish an operation such as band ligation, see U.S. Pat. No. 6,136,009 (Mears) or co-pending U.S. application entitled "Endoscopic Band Ligator" filed Sep. 5, 2003 based on provisional application No. 60/408,555, filed Sep. 6, 2002, each of which are incorporated by reference herein.

The handle 14 is configured to be releasably and slidably mounted onto an endoscope shaft 18 (shown in FIGS. 1A, 1B and in phantom in FIG. 7) and is sized and shaped to permit an operator to simultaneously grasp and control both the handle and mid-portion of the endoscope shaft with one hand. By slightly releasing the user's grip on the handle and shaft, the handle can be slid relative to the endoscope shaft to maintain the handle in a comfortable position relative to the user's body as the endoscope is advanced or withdrawn from the patient.

The control handle 14 may be formed from two molded plastic body halves 80 and 82 shown in FIGS. 8A and 8B. The left body half 80 is shown with handle components assembled in FIG. 7. The assembled handle is slidably and releasably retained on an endoscope shaft 18 by the serpentine arrangement of curved forks 84, 86, 88 and 90 that extend from the body halves to loosely surround the endoscope shaft. When the body halves are assembled, the forks are staggered longitudinally but curve downwardly and around to overlap and define a circumferential pathway thereby, together, providing full circumferential support around the circular endoscope shaft residing within. Still, the forks are staggered sufficiently to permit passage of the shaft when it is angled away from the longitudinal axis of the handle to slip past the fork tips. With the serpentine arrangement of the forks, the handle can be applied to or removed from the endoscope shaft laterally, without requiring removal of end components of the endoscope to slip the handle off the end of the shaft.

Once mounted, the handle 14 can be slid longitudinally along the scope shaft 18 with the physician's right-hand or temporarily restrained in position by grasping the endoscope and handle together between the curved forks. As the handle is slid longitudinally along the endoscope, the sheath 16 freely slides through the sheath guide channel 92 formed through the body of the handle in order to accommodate the corresponding change in distance between the handle and the distal portion 12 of the band ligator. To maintain smooth device operation through the sheath while maintaining free length adjustability, the proximal end 94 of the sheath, joined to the operator controls, is arranged to exit the handle proximal end 96. The sheath then forms a loop 99, reversing its direction, and reenters the handle through the sheath guide channel 92. The sheath is slidably received through sheath guide channel 92 and exits the distal end 98 of the handle and continues distally, outside of the endoscope, to its connection to the distal portion 12 of the band ligator.

The reverse loop configuration prevents bowing of the sheath 16 in the area between the handle and the distal portion 12 of the device, which could cause interference in operating the control wires 53 and 52 through the sheath as well as cause interference in the smooth longitudinal movement of the handle along the endoscope. Instead, as the handle moves longitudinally along the endoscope, sheath 16 slides though sheath guide channel 92, and the size of the loop 99 changes to accommodate the change in distance between handle and distal portion 12. The size of the loop at the proximal side 96 of handle does not interfere with movement of the handle along the endoscope nor does it interfere with the operation of the control wires as the sheath is not forced to bow at the critical area of the proximal end 94, immediately adjacent to its attachment to the control mechanisms. A stop 101 is fixed to the exterior of the sheath to prevent it from being fed too far into the sheath guide channel 92 such that the curvature of the loop 99 becomes excessively tight, possibly impairing operation of the control wires.

Accordingly, from the foregoing, it can be seen that an externally mounted endoscopic accessory control system adaptable to a variety of different endoscopic tools has been presented. It should be understood however, that the foregoing description of the invention is intended merely to be illustrative thereof and that other modifications, embodiments and equivalents may be apparent to those who are skilled in the art without departing from its spirit. Having thus described the invention what we desire to claim and secure by letters patent is:

The invention claimed is:

1. An endoscopic accessory and control system therefor comprising:
   an endoscopic accessory having an operating device mountable to the distal portion of an endoscope;
   a control handle configured to be removably mounted to the shaft of an endoscope;
   the control handle having a proximal end and a distal end;
   a control element extending from the control handle to the operating device, the control handle including at least one operator control associated with the control element by which the control element may be operated to control operation of the operating device;
   the control handle being slidable relative to the control element while remaining operatively connected to the control element;
   the control handle being constructed to enable the user to simultaneously grip and manipulate both the endoscope shaft and the control handle with a single hand;
   one end of the control element extending from the proximal end of the handle and defining a proximally extending loop, the other end of the control element extending from the loop through a guideway in the handle and out of the distal end of the handle, the handle being slidable along the distally extending portion of the control member when the handle and accessory are mounted on the endoscope.

2. An endoscopic accessory and control system as defined in claim 1 wherein the control element extends externally of the endoscope shaft when the operating device and control handle are mounted to the endoscope.

3. An endoscopic accessory and control system as defined in claim 1 wherein the control handle is configured to be mounted laterally onto the endoscope shaft.

4. An endoscopic accessory and control system as defined in claim 3 wherein the control handle is configured to have a plurality of downwardly extending and curved forks that define a circumferential pathway through which an endoscope shaft may be slidably passed.

5. An endoscopic accessory and control system as defined in claim 1 wherein the control handle is configured to enable a user to grasp directly with one hand both the handle and a portion of an endoscope shaft to which the control handle is mounted.

6. An endoscopic accessory and control system as defined in claim 1 wherein the control element includes a sheath and at least two control members extending through the sheath for operating at least two functions of the endoscopic accessory operating device.

7. An endoscopic accessory and control system as defined in claim 1 further comprising, in combination, an endoscope having the operating device mounted on its distal end and the control handle mounted to the shaft of the endoscope, the control element extending externally of the endoscope.

* * * * *